United States Patent [19]
Brasca et al.

[11] Patent Number: 6,057,326
[45] Date of Patent: May 2, 2000

[54] BICYCLIC 4-ARALKYLAMINOPYRIMIDINE DERIVATIVES AS TYROSINE KINASE INHIBITORS

[75] Inventors: Maria Gabriella Brasca, Cusago; Dario Ballinari, San Donato Milanese; Antonio Longo, Milan; Franco Buzzetti, Monza, all of Italy

[73] Assignee: Pharmacia & Upjohn S.p.A, Milan, Italy

[21] Appl. No.: 09/000,238

[22] PCT Filed: Jun. 3, 1997

[86] PCT No.: PCT/EP97/02965

§ 371 Date: Feb. 6, 1998

§ 102(e) Date: Feb. 6, 1998

[87] PCT Pub. No.: WO97/49689

PCT Pub. Date: Dec. 31, 1997

[30] Foreign Application Priority Data

Jun. 21, 1996 [GB] United Kingdom .................. 9613021

[51] Int. Cl.[7] ............... C07D 239/94; C07D 473/34; A61K 31/70; A61K 31/505
[52] U.S. Cl. ............... 514/259; 544/293; 544/284
[58] Field of Search ................... 544/293, 284; 514/259

[56] References Cited

U.S. PATENT DOCUMENTS

| | | | |
|---|---|---|---|
| 5,296,484 | 3/1994 | Coghlan et al. | 514/311 |
| 5,576,330 | 11/1996 | Buzzetti et al. | 514/307 |
| 5,652,250 | 7/1997 | Buzzetti et al. | 514/352 |
| 5,656,654 | 8/1997 | Buzzetti et al. | 514/412 |
| 5,663,346 | 9/1997 | Buzzetti et al. | 546/113 |
| 5,719,135 | 2/1998 | Buzzetti et al. | 514/81 |

FOREIGN PATENT DOCUMENTS

| | | |
|---|---|---|
| 326328 | 8/1989 | European Pat. Off. . |
| 390112 | 10/1990 | European Pat. Off. . |
| 04235976 | 8/1992 | Japan . |
| 06172321 | 6/1994 | Japan . |
| WO 95/19774 | 7/1995 | WIPO . |

*Primary Examiner*—Richard L. Raymond
*Assistant Examiner*—Hong Liu
*Attorney, Agent, or Firm*—Oblon, Spivak, McClelland, Maier & Neustadt, P.C.

[57] ABSTRACT

Novel and known bicyclic 4-aralkylaminopyrimidine derivatives of formula (I) wherein A is a benzene or imidazole ring; B is a benzene, tetralin, indane or 2-oxindole ring R is $(C_1-C_4)$perfluoroalkyl, phenyl, phenyl-$(C_1-C_4)$alkyl, hydroxy-$(C_1-C_4)$alkyl, $(C_1-C_4)$alkoxy-$(C_1-C_4)$alkyl, $(C_2-C_4)$acyloxy-$(C_1-C_4)$alkyl, halobenzoyloxy-$(C_1-C_4)$alkyl, carboxy, carbamoyl, $(C_1-C_4)$alkoxycarbonyl, cyano, $(C_1-C_4)$alkylcarbonyl, carboxy-$(C_1-C_4)$alkyl, carbamoyl-$(C_1-C_4)$alkyl, $(C_1-C_4)$alkoxycarbonyl-$(C_1-C_4)$alkyl, halo-$(C_1-C_4)$alkyl, amino-$(C_1-C_4)$alkyl, mono- or di-$(C_1-C_4)$alkylamino-$(C_1-C_4)$alkyl, sulfo-$(C_1-C_4)$alkyl or sulfamido-$(C_1-C_4)$alkyl; each of $R_1$ and $R_2$, which may be the same or different, is hydrogen, $C_1-C_4$ alkyl, $C_1-C_4$ alkoxy, halogen or —$NR_5R_6$ in which each of $R_5$ and $R_6$, which may be the same or different, is H or $C_1-C_4$ alkyl; each of $R_3$ and $R_4$, which may the same or different, is hydrogen, $C_1-C_4$ alkyl, halogen, hydroxy, $C_1-C_4$ alkoxy, $C_1-C_4$ alkoxycarbonyl, nitro, cyano or $CF_3$; and the pharmaceutically acceptable salts thereof, are tyrosine kinase inhibitors.

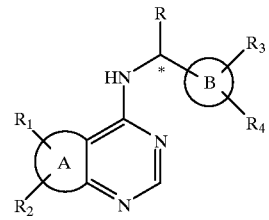

(I)

10 Claims, No Drawings

BICYCLIC 4-ARALKYLAMINOPYRIMIDINE DERIVATIVES AS TYROSINE KINASE INHIBITORS

This application is a 371 of PCT/EP97/02965, filed Jun. 3, 1997.

The present invention relates to novel and known bicyclic 4-aralkylaminopyrimidine derivatives, to a process for their preparation, to pharmaceutical compositions containing them and to their use as therapeutic agents, in particular as tyrosine kinase inhibitors.

Several N-substituted 4-aminopyrimidines are known in the art. For instance Japanese patent application JP92-270490 (C.A. 122: 133208) discloses the preparation of N-substituted 4-amino-pyrimidine derivatives useful as agrochemical fungicides, insecticides, nematocides and acaricides. French patent no. 1438006 (C.A.66: 11176e) claims 6-substituted purine compounds having kinetine activity. EP-A-0390112 discloses purine and pyrazolo-pyrimidine compounds which are selective adenosine receptor agents in particular adenosine antagonists. Phytochemistry 10(1), 23-8, 1971; and ibidem, 7(11), 1989–94, 1968 relate to cytokinin activity of substituted purines in plants. DE 4321029 (C.A.122: 160674) teaches the preparation of 4-substituted quinazolineamines useful as agrochemical fungicides.

The present invention provides, as a first aspect, the use of a compound having the following formula (I)

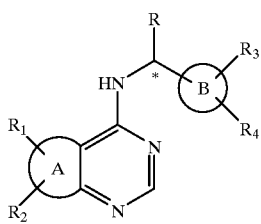

wherein
A is a benzene or imidazole ring;
B is a benzene, tetralin, indane or 2-oxindole ring;
R is $(C_1-C_4)$ perfluoroalkyl, phenyl, phenyl-$(C_1-C_4)$alkyl, hydroxy-$(C_1-C_4)$alkyl, $(C_1-C_4)$alkoxy-$(C_1-C_4)$alkyl, $(C_2-C_4)$acyloxy-$(C_1-C_4)$alkyl, halobenzoyloxy-$(C_1-C_4)$alkyl, carboxy, carbamoyl, $(C_1-C_4)$alkoxycarbonyl, cyano, $(C_1-C_4)$alkylcarbonyl, carboxy-$(C_1-C_4)$alkyl, carbamoyl-$(C_1-C_4)$alkyl, $(C_1-C_4)$alkoxycarbonyl-$(C_1-C_4)$alkyl, halo-$(C_1-C_4)$alkyl, amino-$(C_1-C_4)$alkyl, mono- or di-$(C_1-C_4)$alkylamino-$(C_1-C_4)$alkyl, sulfo-$(C_1-C_4)$alkyl or sulfamido-$(C_1-C_4)$alkyl;
each of $R_1$ and $R_2$, independently, is hydrogen, $C_1-C_4$ alkyl, $C_1-C_4$ alkoxy, halogen or —$NR_5R_6$ in which each of $R_5$ and $R_6$ independently is H or $C_1-C_4$ alkyl;
each of $R_3$ and $R_4$, independently, is hydrogen, $C_1-C_4$ alkyl, halogen, hydroxy, $C_1-C_4$ alkoxy, $C_1-C_4$ alkoxycarbonyl, nitro, cyano or $CF_3$; or a pharmaceutically acceptable salt thereof, for the manufacture of a medicament for use as tyrosine kinase inhibitor.

It is evident to the people skilled in the art that when at the same time ring A is imidazole and one of $R_1$ and $R_2$ is $C_1-C_4$ alkoxy, halogen or —$NR_5R_6$ then such substituent is only linked to the carbon ring atoms of the imidazole moiety. Whereas when the substituents $R_1$ and $R_2$ are $C_1-C_4$ alkyl they may be attached either to the carbon or nitrogen ring atoms of the imidazole moiety.

When the ring B is tetralin, indane or 2-oxindole the aminomethyl bridge may be located on either of the ring B moieties, preferably it is located on the benzene moiety.

The $R_3$ and $R_4$ substituents in tetralin and indane may be on either of the ring moieties, preferably they are attached to the benzene moiety. In 2-oxindole the $R_3$ and $R_4$ substituents can be located on the benzene moiety, whereas the $C_1-C_4$ alkyl substituent may also be attached to the nitrogen ring atom of the pyrrole moiety, of course.

When in the synthesis optically active aralkylamino derivatives are employed, then the R substituent may be above or beneath the plane indicating an (R) or (S) configuration.

The invention includes within its scope all the possible isomers, stereoisomers and their mixtures, and the metabolites and the metabolic precursors or bio-precursors (otherwise known as prodrugs) of the compounds of formula (I).

An alkyl group or an alkyl moiety in a alkoxy, alkylcarbonyl or alkoxycarbonyl group may be a branched or straight alkyl chain.

A $C_1-C_4$ alkyl group is preferably a $C_1-C_2$ alkyl, that is ethyl or methyl.

A $C_1-C_4$ alkoxy group is preferably a methoxy or ethoxy group.

A $C_1-C_4$ alkylcarbonyl is preferably an acetyl.
A $(C_1-C_4)$perfluoralkyl is preferably a trifluoromethyl.
A phenyl-$(C_1-C_4)$alkyl is preferably benzyl.
A hydroxy-$(C_1-C_4)$alkyl is preferably hydroxymethyl.
A $(C_1-C_4)$alkoxy-$(C_1-C_4)$alkyl is preferably methoxymethyl.
An $(C_2-C_4)$acyloxy-$(C_1-C_4)$alkyl is preferably acetoxymethyl.
A halobenzoyloxy-$(C_1-C_4)$alkyl is preferably a bromobenzoyloxy-$(C_1-C_4)$alkyl, in particular, bromobenzoyloxymethyl.
A $(C_1-C_4)$alkoxycarbonyl is preferably carbomethoxy.
A halo-$(C_1-C_4)$alkyl is preferably chloromethyl.
A mono-$(C_1-C_4)$alkylamino-$(C_1-C_4)$alkyl is preferably methylaminomethyl.
A di-$(C_1-C_4)$alkylamino-$(C_1-C_4)$alkyl is preferably dimethylaminomethyl.
A sulfamido-$(C_1-C_4)$alkyl is preferably sulfamidomethyl.
A halogen atom is for example fluoro, chloro, bromo or iodio, in particular bromo or fluoro.

Pharmaceutically acceptable salts of the compounds of the i invention include acid addition salts with inorganic acids, e.g. nitric, hydrochloric, hydrobromic, sulphuric, perchloric and phosphoric acid or organic acids, e.g. acetic, trifluoracetic, propionic, glycolic, lactic, oxalic, malonic, malic, maleic, tartaric, citric, benzoic, cinnamic, mandelic and salicylic acid. The salts with inorganic bases include e.g. alkali metal, especially sodium or potassium bases, or earth alkali metal, especially calcium or magnesium bases, or with organic bases, e.g. alkylamines, preferably triethylamine.

As stated above, the present invention also includes within its scope pharmaceutically acceptable bio-precursors [otherwise known as prodrugs of the compounds of formula (I)], i.e. compounds which have different formula to formula (I) above but which, nevertheless, upon administration to a human being are converted directly or indirectly in vivo into a compound of formula (I).

Preferred compounds of the invention are the compounds of formula (I), wherein
A is a benzene or imidazole ring;
B is a benzene or tetralin ring;
R is hydroxy-$(C_1-C_4)$alkyl, $(C_2-C_4)$acyloxy-$(C_1-C_4)$alkyl, halobenzoyloxy-$(C_1-C_4)$alkyl, $(C_1-C_4)$alkoxycarbonyl, di-$(C_1-C_4)$alkylamino-$(C_1-C_4)$alkyl, trifluoromethyl or carbamoyl;

each of $R_1$ and $R_2$ independently is hydrogen or $C_1$–$C_4$-alkoxy;
each of $R_3$ and $R_4$ is hydrogen;
and the pharmaceutically acceptable salts thereof.

Examples of preferred specific compounds of formula (I) are the following compounds:

4-[α-(hydroxymethyl)benzylamino]-6,7-dimethoxyquinazoline;
4-[α-(acetoxymethyl)benzylamino]-6,7-dimethoxyquinazoline;
4-[α-(3-bromobenzoyloxymethyl)benzylamino]-6,7-dimethoxyquinazoline;
4-[α-(trifluoromethyl)benzylamino]-6,7-dimethoxyquinazoline;
4-[α-(carbamoyl)benzylamino]-6,7-dimethoxyquinazoline;
4-[α-(carbomethoxy)benzylamino]-6,7-dimethoxyquinazoline;
4-[α-(dimethylaminomethyl)benzylamino]-6,7-dimethoxyquinazoline
4-[α-(hydroxymethyl)-2-tetralylmethylamino]-6,7-dimethoxyquinazoline;
4-[α-(acetoxymethyl)-2-tetralylmethylamino]-6,7-dimethoxyquinazoline;
4-[α-(3-bromobenzoyloxymethyl)-2-tetralylmethylamino]-6,7dimethoxyquinazoline;
4-[α-(trifluoromethyl)-2-tetralylmethylamino]-6,7-dimethoxyquinazoline;
4-[α-(carbamoyl)-2-tetralylmethylamino]-6,7-dimethoxyquinazoline;
4-[α-(carbomethoxy)-2-tetralylmethylamino]-6,7-dimethoxyquinazoline;
4-[α-(dimethylaminomethyl)-2-tetralylmethylamino]-6,7dimethoxy-quinazoline;
6-[α-(hydroxymethyl)benzylamino]-purine;
6-[α-(acetoxymethyl)benzylamino]-purine;
6-[α-(3-bromobenzoyloxymethyl)benzylamino]-purine;
6-[α-(trifluoromethyl)benzylamino]-purine;
6-[α-(carbamoyl)benzylamino]-purine;
6-[α-(carbomethoxy)benzylamino]-purine;
6-[α-(dimethylaminomethyl)benzylamino]-purine;
6-[α-(hydroxymethyl)-2-tetralylmethylamino]-purine;
6-[α-(acetoxymethyl)-2-tetralylmethylamino]-purine;
6-[α-(3-bromobenzoyloxymethyl)-2-tetralylmethylamino]-purine;
6-[α-(trifluoromethyl)-2-tetralylmethylamino]-purine;
4-[α-(carbamoyl)-2-tetralylmethylamino]-purine;
4-[α-(carbomethoxy)-2-tetralylmethylamino]-purine; and
4-[α-(dimethylaminomethyl)-2-tetralylmethylamino]-purine;

either as single isomers or as a mixture thereof and the pharmaceutically acceptable salts thereof.

Accordingly, the present invention provides a method of treating a mammal, including humans, in need of a tyrosine kinase inhibiting agent, the method comprising administering to said mammal a therapeutically effective amount of a compound of formula (I) or a pharmaceutically acceptable salt thereof.

A further object of the present invention is to provide a pharmaceutical composition comprising a pharmaceutically acceptable excipient (which can be a carrier and/or diluent) and as an active principle a compound of formula (IA)

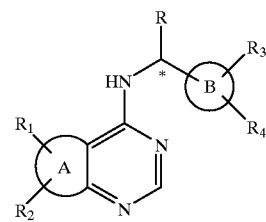

(IA)

wherein
A is a benzene or imidazole ring;
B is a benzene, tetralin, indane or 2-oxindole ring;
R is ($C_1$–$C_4$) perfluoroalkyl, phenyl, phenyl-($C_1$–$C_4$)alkyl, hydroxy-($C_1$–$C_4$)alkyl, ($C_1$–$C_4$)alkoxy-($C_1$–$C_4$)alkyl, ($C_2$–$C_4$)acyloxy-($C_1$–$C_4$)alkyl, halobenzoyloxy-($C_1$–$C_4$)alkyl, carboxy, carbamoyl, ($C_1$–$C_4$)alkoxycarbonyl, cyano, ($C_1$–$C_4$)alkylcarbonyl, carboxy-($C_1$–$C_4$)alkyl, carbamoyl-($C_1$–$C_4$)alkyl, ($C_1$–$C_4$)alkoxycarbonyl-($C_1$–$C_4$)alkyl, halo-($C_1$–$C_4$)alkyl, amino-($C_1$–$C_4$)alkyl, mono- or di-($C_1$–$C_4$)alkylamino-($C_1$–$C_4$)alkyl, sulfo-($C_1$–$C_4$)alkyl or sulfamido-($C_1$–$C_4$)alkyl;
each of $R_1$ and $R_2$, independently, is hydrogen, $C_1$–$C_4$ alkyl, $C_1$–$C_4$ alkoxy, halogen or —$NR_5R_6$ in which each of $R_5$ and $R_6$ independently is H or $C_1$–$C_4$ alkyl ;
each of $R_3$ and $R_4$, independently, is hydrogen, $C_1$–$C_4$ alkyl, halogen, hydroxy, $C_1$–$C_4$ alkoxy, $C_1$–$C_4$ alkoxycarbonyl, nitro, cyano or $CF_3$; or a pharmaceutically acceptable salt thereof, and wherein when at the same time A is unsubstituted imidazole and B is unsubstituted phenyl, then R is other than hydroxy-($C_1$–$C_3$)alkyl.

Preferred compounds of formula (IA), as defined above, are those wherein
A is a benzene or imidazole ring;
B is a benzene or tetralin ring;
R is hydroxy-($C_1$–$C_4$)alkyl, ($C_2$–$C_4$)acyloxy-($C_1$–$C_4$)alkyl, halobenzoyloxy-($C_1$–$C_4$)alkyl, ($C_1$–$C_4$)alkoxycarbonyl, di-($C_1$–$C_4$)alkylamino-($C_1$–$C_4$)alkyl, trifluoromethyl or carbamoyl;
each of $R_1$ and $R_2$ independently is hydrogen or $C_1$–$C_4$ alkoxy;
each of $R_3$ and $R_4$ is hydrogen;
and the pharmaceutically acceptable salts thereof.

Examples of preferred specific compounds of formula (IA) are the following compounds:
4-[α-(hydroxymethyl)benzylamino]-6,7-dimethoxyquinazoline;
4-[α-(acetoxymethyl)benzylamino]-6,7-dimethoxyquinazoline;
4-[α-(3-bromobenzoyloxymethyl)benzylamino]-6,7-dimethoxyquinazoline;
4-[α-(trifluoromethyl)benzylamino]-6,7-dimethoxyquinazoline;
4-[α-(carbamoyl)benzylamino]-6,7-dimethoxyquinazoline;
4-[α-(carbomethoxy)benzylamino]-6,7-dimethoxyquinazoline;
4-[α-(dimethylaminomethyl)benzylamino]-6,7-dimethoxyquinazoline;
4-[α-(hydroxymethyl)-2-tetralylmethylamino]-6,7-dimethoxyquinazoline;
4-[α-(acetoxymethyl)-2-tetralylmethylamino]-6,7-dimethoxyquinazoline;
4-[α-(3-bromobenzoyloxymethyl)-2-tetralylmethylamino]-6,7dimethoxyquinazoline;
4-[α-(trifluoromethyl)-2-tetralylmethylamino]-6,7-dimethoxyquinazoline;

4-[α-(carbamoyl)-2-tetralylmethylamino]-6,7-dimethoxyquinazoline;
4-[α-(carbomethoxy)-2-tetralylmethylamino]-6,7-dimethoxyquinazoline;
4-[α-(dimethylaminomethyl)-2-tetralylmethylamino]-6,7dimethoxyquinazoline;
6-[α-(acetoxymethyl)benzylamino]-purine;
6-[α-(3-bromobenzoyloxymethyl)benzylamino]-purine;
6-[α-(trifluoromethyl)benzylamino]-purine;
6-[α-(carbamoyl)benzylamino]-purine;
6-[α-(carbomethoxy)benzylamino]-purine;
6-[α-(dimethylaminomethyl)benzylamino]-purine;
6-[α-(hydroxymethyl)-2-tetralylmethylamino]-purine;
6-[α-(acetoxymethyl)-2-tetralylmethylamino]-purine;
6-[α-(3-bromobenzoyloxymethyl)-2-tetralylmethylamino]-purine;
6-[α-(trifluoromethyl)-2-tetralylmethylamino]-purine;
4-[α-(carbamoyl)-2-tetralylmethylamino]-purine;
4-[α-(carbomethoxy)-2-tetralylmethylamino]-purine; and
4-[α-(dimethylaminomethyl)-2-tetralylmethylamino]-purine;
either as single isomers or as a mixture thereof and the pharmaceutically acceptable salts thereof.

Another object of the present invention is to provide a bicyclic 4-aralkylaminopyrimidine derivative of formula (IA), or a pharmaceutically acceptable salt thereof, as defined above, for use as an active therapeutic substance, in particular as tyrosine kinase inhibitor.

A further object of the invention are novel bicyclic 4-aralkylaminopyrimidine derivatives having the following formula (IB)

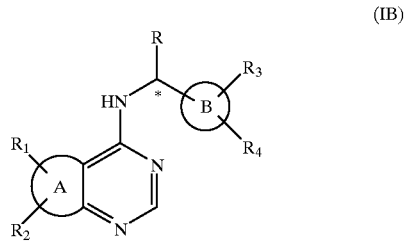

(IB)

wherein
A is a benzene or imidazole ring;
B is a benzene, tetralin, indane or 2-oxindole ring;
R is $(C_1–C_4)$ perfluoroalkyl, phenyl, phenyl-$(C_1–C_4)$alkyl, hydroxy-$(C_1–C_4)$alkyl, $(C_1–C_4)$alkoxy-$(C_1–C_4)$alkyl, $(C_2–C_4)$acyloxy-$(C_1–C_4)$alkyl, halobenzoyloxy-$(C_1–C_4)$alkyl, carboxy, carbamoyl, $(C_1–C_4)$alkoxycarbonyl, cyano, $(C_1–C_4)$alkylcarbonyl, carboxy-$(C_1–C_4)$alkyl, carbamoyl-$(C_1–C_4)$alkyl, $(C_1–C_4)$alkoxycarbonyl-$(C_1–C_4)$alkyl, halo-$(C_1–C_4)$alkyl, amino-$(C_1–C_4)$alkyl, mono- or di-$(C_1–C_4)$alkylamino-$(C_1–C_4)$alkyl, sulfo-$(C_1–C_4)$alkyl or sulfamido-$(C_1–C_4)$alkyl;
each of $R_1$ and $R_2$, independently, is hydrogen, $C_1–C_4$ alkyl, $C_1–C_4$ alkoxy, halogen or —$NR_5R_6$ in which each of $R_5$ and $R_6$ independently is H or $C_1–C_4$ alkyl ;
each of $R_3$ and $R_4$, independently, is hydrogen, $C_1–C_4$ alkyl, halogen, hydroxy, $C_1–C_4$ alkoxy, $C_1–C_4$ alkoxycarbonyl, nitro, cyano or $CF_3$; or a pharmaceutically acceptable salt thereof,
and wherein when at the same time, A is unsubstituted benzene or imidazole, R is hydroxyethyl, $(C_1–C_4)$alkoxy-ethyl or $(C_2–C_4)$acyloxy-ethyl, and B is phenyl, then at least one of
$R_3$ and $R_4$ is other than hydrogen, halogen, $C_1–C_4$ alkyl or $C_1–C_4$ alkoxy; and wherein, when at the same time A is unsubstituted imidazole and B is unsubstituted phenyl, then R is other than carboxy or hydroxy-$(C_1–C_3)$alkyl.

Preferred compounds of formula (IB), as defined above, are those wherein
A is a benzene or imidazole ring;
B is a benzene or tetralin ring;
R is hydroxy-$(C_1–C_4)$alkyl, $(C_2–C_4)$acyloxy-$(C_1–C_4)$alkyl, halobenzoyloxy-$(C_1–C_4)$alkyl, $(C_1–C_4)$alkoxycarbonyl, di-$(C_1–C_4)$alkylamino-$(C_1–C_4)$alkyl, trifluoromethyl or carbamoyl;
each of $R_1$ and $R_2$ independently is hydrogen or $C_1–C_4$ alkoxy;
each of $R_3$ and $R_4$ is hydrogen;
and the pharmaceutically acceptable salts thereof.

Examples of preferred specific compounds of formula (IB) are the following compounds:
4-[α-(hydroxymethyl)benzylamino]-6,7-dimethoxyquinazoline;
4-[α-(acetoxymethyl)benzylamino]-6,7-dimethoxyquinazoline;
4-[α-(3-bromobenzoyloxymethyl)benzylamino]-6,7-dimethoxyquinazoline;
4-[α-(trifluoromethyl)benzylamino]-6,7-dimethoxyquinazoline;
4-[α-(carbamoyl)benzylamino]-6,7-dimethoxyquinazoline;
4-[α-(carbomethoxy)benzylamino]-6,7-dimethoxyquinazoline;
4-[α-(dimethylaminomethyl)benzylamino]-6,7-dimethoxyquinazoline;
4-[α-(hydroxymethyl)-2-tetralylmethylamino]-6,7-dimethoxyquinazoline;
4-[α-(acetoxymethyl)-2-tetralylmethylamino]-6,7-dimethoxyquinazoline;
4-[α-(3-bromobenzoyloxymethyl)-2-tetralylmethylamino]-6,7dimethoxyquinazoline;
4-[α-(trifluoromethyl)-2-tetralylmethylamino]-6,7-dimethoxyquinazoline;
4-[α-(carbamoyl)-2-tetralylmethylamino]-6,7-dimethoxyquinazoline;
4-[α-(carbomethoxy)-2-tetralylmethylamino]-6,7-dimethoxyquinazoline;
4-[α-(dimethylaminomethyl)-2-tetralylmethylamino]-6,7dimethoxyquinazoline;
6-[α-(acetoxymethyl)benzylamino]-purine;
6-[α-(3-bromobenzoyloxymethyl)benzylamino]-purine;
6-[α-(trifluoromethyl)benzylamino]-purine;
6-[α-(carbamoyl)benzylamino]-purine;
6-[α-(carbomethoxy)benzylamino]-purine;
6-[α-(dimethylaminomethyl)benzylamino]-purine;
6-[α-(hydroxymethyl)-2-tetralylmethylamino]-purine;
6-[α-(acetoxymethyl)-2-tetralylmethylamino]-purine;
6-[α-(3-bromobenzoyloxymethyl)-2-tetralylmethylamino]-purine;
6-[α-(trifluoromethyl)-2-tetralylmethylamino]-purine;
4-[α-(carbamoyl)-2-tetralylmethylamino]-purine;
4-[α-(carbomethoxy)-2-tetralylmethylamino]-purine; ana
4-[α-(dimethylaminomethyl)-2-tetralylmethylamino]-purine;
either as single isomers or as a mixture thereof and pharmaceutically acceptable salts thereof.

Another object of the present invention is to provide a novel bicyclic 4-aralkylaminopyrimidine derivative of formula (IB), or a pharmaceutically acceptable salt thereof, as defined above, for use as an active therapeutic substance, in particular as tyrosine kinase inhibitor.

Object of the invention is also a pharmaceutical composition comprising a compound of formula (IB), or a pharmaceutically acceptable salt thereof, as defined above, as an active principle and a pharmaceutically acceptable excipient (which can be a carrier and/or diluent).

The compounds of formula (I), (IA), (IB) and the pharmaceutically acceptable salts thereof, are altogether defined hereafter as the "compounds of the invention" or as the "active agents" of the invention.

The novel compounds of formula (IB) and the known ones of formula (I) and (IA) can be similarly obtained by the same analogy process. For instance the novel compounds of formula (IB) and the salts thereof can be obtained by a process comprising the condensation of a compound of formula (II)

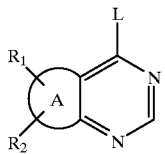

(II)

wherein A, $R_1$ and $R_2$ are as defined above and L is a leaving group with an amine compound of formula (III)

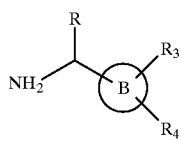

(III)

wherein B, R, $R_3$ and $R_4$ are as defined above; and, if desired, converting a compound of formula (IB) into another compound of formula (IB), and/or, if desired, converting a compound of formula (IB) into a salt thereof, and/or, if desired, converting a salt of a compound of formula (IB) into a free compound of formula (IB), and/or, if desired, separating a mixture of isomers of a compound of formula (IB) into the single isomers.

A leaving group in a compound of formula (II) is for instance chloro, methylthio and 1,2,4-triazol-1-yl.

The reaction of a compound of formula (II) wherein L is chloro with a compound of formula (III) is an analogy process, which can be carried out using known methods, e.g. as described by Bullock et al. in J.Am.Chem.Soc. 78, 3693 (1956). The reaction is carried out in the presence of a suitable inert organic solvent, for example an alkanol or ester such as methanol, ethanol, isopropanol, methyl cellosolve or ethyl acetate, a halogenated solvent such as dichloromethane or chloroform, an ether such as tetrahydrofuran or dioxane, a dipolar aprotic solvent such as dimethylformamide or dimethylacetamide. Preferably the solvents isopropanol or methyl cellosolve are used. The reaction is conveniently carried out at a temperature in the range from about 10 to about 150° C., preferably in the range from about 20 to about 80° C. In general only 1 equivalent of amine compound (III) is used, thus giving the hydrochloride salt, which precipitates on cooling. To obtain the free base of the compound of formula (IB) from the salt, the salt may be treated with a suitable base in the presence of an appropriate solvent such as the ones mentioned above. Suitable bases are e.g. organic amines such as triethylamine or pyridine, or inorganic bases such as sodium carbonate or sodium hydroxide. Alternatively to obtain directly the free base of formula (IB) one may apply more than 2 equivalent of amine compound (III) in the reaction.

The reaction of a compound of formula (II), wherein L is 1,2,4-triazol-1-yl, with a compound of formula (III) can be carried out according to known methods, e.g. as described in EP 0414386. Accordingly, about 1 molequivalent of triazolyl compound II and about 1 molequivalent of amine compound (III) is reacted at reflux temperature in an inert organic solvent such as chloroform, methylenechloride, benzene or toluene. After about 2 h an organic base such triethylamine is added and the reflux is continued for about 2 h.

The optional salification of a compound of formula (IB) as well as the conversion of the salt into the corresponding free compound and the separation of the mixture of isomers into the single isomers as well as the conversion of a compound of formula (IB) into another compound of formula (IB) may be carried according to known methods.

The conversion of a compound of formula (IB), wherein $R_1$ or $R_2$ is halogen, into a compound of formula (IB), wherein $R_1$ or $R_2$ is $NR_5R_6$, can be carried out by known methods, e.g. according to the method of Bullock et al [J.Am.Chem.Soc. 78,3693 (1956)] as described above.

The conversion of a compound of formula (IB), wherein $R_1$ or $R_2$ is halogen, into a compound of formula (IB), wherein $R_1$ or $R_2$ is $C_1$–$C_4$ alkoxy, can be carried out by using known methods. For example to obtain the $C_1$–$C_4$ alkoxy derivative, the corresponding halogen derivative is reacted with an alkali $C_1$–$C_4$ alkanoate (prepared by adding an alkali metal to the corresponding $C_1$–$C_4$ alkanol) in $C_1$–$C_4$ alkanol solution at temperatures ranging from about 50 to about 100° C. in a pressure vessel.

The conversion of a compound of formula (IB) wherein R is hydroxy-($C_1$–$C_4$)alkyl into a compound of formula (IB) wherein R is ($C_2$–$C_4$)acyloxy-($C_1$–$C_4$)alkyl or halobenzoyloxy-($C_1$–$C_4$) alkyl, can be carried out by using known methods, e.g. by reaction with a reactive derivative of a suitable carboxylic acid, such as an anhydride or halide, in the presence of a basic agent, at temperatures ranging from about 0 to about 50° C. Preferably the acylation is carried out by reaction with the respective acid anhydride or chloride in the presence of an organic base such as pyridine.

The conversion of a compound of formula (IB) wherein R is hydroxy-($C_1$–$C_4$)alkyl into a compound of formula (IB) wherein R is ($C_1$–$C_4$)alkoxy-($C_1$–$C_4$)alkyl, can be carried out by known methods. According to the Williamson reaction (for a review see Patai: The chemistry of the ether linkage, Interscience Publisher NY 1967) the alcohol is first transformed into alkali metal alkoxide, preferably by reaction with sodium hydride, which is then reacted with an ($C_1$–$C_4$)alkylhalide, preferably an ($C_1$–$C_4$)alkyliodide, in an inert organic solvent such as benzene.

The conversion of a compound of formula (IB) wherein R is halo-($C_1$–$C_4$)alkyl into a compound of formula (IB) wherein R is ($C_1$–$C_4$)alkylamino-($C_1$–$C_4$)alkyl, can be carried out by known methods, e.g. as described in Houben-Weyl, Methoden der Organischen Chemie, volume XI/1, page 24(1957). Accordingly, the halocompound, preferably a iodo or bromine compound, is reacted with an ($C_1$–$C_4$) alkylamine (preferably using an excess) in an inert solvent such as water or alkohol at temperatures ranging from about 0 to about 100° C.

A compound of formula (IB) wherein R is ($C_1$–$C_4$) alkoxycarbonyl-($C_1$–$C_4$)alkyl can be obtained by conversion (esterification) of a compound of formula (IB) wherein R is carboxy-($C_1$–$C_4$)alkyl by using known methods, e.g. as described in Houben-Weyl: Methoden Organischen Chemie VIII, 508 (1952). Thus the acid compound is reacted with an excess of an ($C_1$–$C_4$)alcohol in an inert solvent such as chloroform or benzene at temperatures ranging from room to reflux temperatures in the presence of a mineral acid catalyst such as sulfuric or hydrochloric acid.

The conversion of a compound of formula (IB) wherein R is a $(C_1-C_4)$alkoxycarbonyl-$(C_1-C_4)$alkyl, preferably carbomethoxy-$(C_1-C_4)$alkyl, into a compound of formula (IB) wherein R is carbamoyl-$(C_1-C_4)$alkyl, may be carried out by aminolysis, e.g. as described in Houben-Weyl: Methoden der Organischen Chemie, volume E5, part 2, page 983 (1985).

The compounds of formula (II) are known or may be obtained by known methods from known compounds. For example the 4-chloro compound of formula (II) wherein L is chloro is prepared by chlorodehydroxylation of the corresponding 4-hydroxypyrimidine derivative of formula (IV)

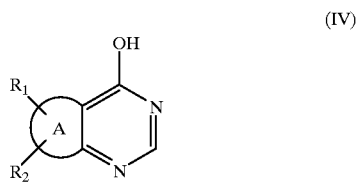

(IV)

wherein A, $R_1$ and $R_2$ are as defined above, by using conventional methods, e.g. by reaction with $POCl_3$ or $SOCl_2$. For example the preparation of 4-chloro-6,7-dimethoxyquinazoline from 4-hydroxy-6,7-dimethoxyquinazoline is described in example 1 of patent AU9331010.

The intermediate of formula (II), wherein L is 1,2,4-triazol-1-yl, can be prepared, e.g. by adding gradually $POCl_3$ to a mixture of compound (IV) (1 equivalent) and 1,2,4-triazole (3 equivalent) in pyridine solution at a temperature ranging from room to reflux temperature.

The compounds of formula (IV) are commercially available or may be obtained by known methods from known compounds. A general applicable method for the synthesis of compounds of formula (V) in which A is benzene is to condense an anthranilic acid derivative of formula (V):

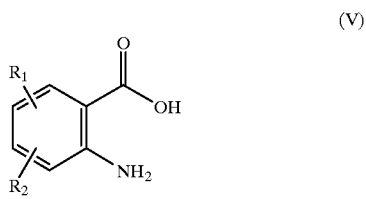

(V)

wherein $R_1$ and $R_2$ are as defined above, with an excess of formamide at temperatures ranging from 170 to 200° C. The compounds of formula (V) are known or may be obtained by known methods from known compounds.

When in the new compounds of the present invention and in the intermediate products used for their preparation there are groups present which need to be protected before the above-described reactions are performed, they may be protected before the reaction takes place and then deprotected at the end of the reaction, according to well known methods in organic chemistry.

Pharmacology

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence, the compounds according to the present invention can be useful in the treatment of pathological proliferation disorders in mammals, including humans. Typical examples of such disorders are tumors, including leukemia, and psoriasis. The compounds of the invention can also be useful in inhibiting the development of the atheromatous plaque and in the control of angiogenesis and as anti-metastatic agents.

Recent studies on the molecular basis of the neoplastic transformation have identified a family of genes, designed oncogenes, whose aberrant expression causes tumorigenesis. For example, the RNA tumor viruses possess such an oncogene sequence whose expression determines neoplastic conversion of infected cells. Several of their oncogene-encoded proteins, such as $pp_{60}^{v-src}$, $p70^{gag-yes}$, $p130^{gag-fps}$ and $p_{70}^{gag-fgr}$ display protein tyrosine kinase activity, that is they catalyze the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity. Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinase can be useful in investigating the mechanism of cancerogenesis, cell proliferation and differentiation and it can be effective in the prevention and chemotherapy of cancer and in other pathological proliferative conditions.

Hence the compounds according to the present invention can be useful in the treatment of pathological proliferation disorders in mammals, including humans.

A human or animal, e.g. a mammal, can thus be treated by a method comprising the administration thereto of a therapeutically effective amount of one of the compounds of the invention. In this way the condition of the human or animal may be improved. Amelioration of the disease state or disorder from which the human or animal is suffering can be achieved. Typical examples of such disorders are benign and malignant tumours, including leukemia such as myeloblastic leukaemia, lymphoma, sarcoma, neuroblastoma, Wilm's tumour, malignant neoplasm of the bladder, breast, lung or thyroid, neoplasias of epithelial origin, such as mammacarcinoma. Moreover, they can be useful in the treatment of epidermal hyperproliferation, such as psoriasis. The compounds of the invention can also be useful in inhibiting the development of the atheromatous plaque and restenosis, in the control of angiogenesis, as anti-metastatic agents and in treating diabetic complications. They have also utility in the control of immune system diseases, e.g. as immunosuppressants, as far as protein tyrosine kinases, particularly Zap70, p56 lck and p59 fyn, are strongly involved in the control of the proliferation of the immune system. Moreover, the compounds of the invention have utility in the treatment of Alzheimer's disease due to the pivotal role played by tyrosine phosphorylation (e.g. Tau proteins) in the development of the disease.

The tyrosine specific protein kinase activity of the compounds of the invention is shown, e.g., by the fact that they are active in the in vitro and in vivo test described herebelow.

EGFR-Autophosphorylation Assay (AMIKA assay)

The EGFR autophosphorylation was assayed using A431 crude membrane extracts as source of the receptor.

Membrane purification:

Membranes were prepared as reported by A. Levitzky et al. (Methods in Enzymology 201, 347 (1991) with minor modifications and adapting the method to the A431 human epidermoid carcinoma cell line. Briefly, low density cells growing in RPMI 1640 plus 10% foetal calf serum were detached using 1 mM EDTA in phosphate buffer saline (PBS) and lysed in cold Lysing buffer (1 ml/$10^6$cells) (20 mM HEPES pH 7.6, 10 mM NaCl, 2 mM EDTA, 10 mg/ml Aprotinin, 10 mg/ml Luepeptin, 1 mM PMSF). Cells were homogenized by 10 strokes in Dounce homogenizer. Nuclei and debris were removed by low speed centrifugation. Membranes were pelletized by ultracentrifugation (1 h, 100000×g) and resuspended in cold HNG buffer (50 mM HEPES pH 7.6, 125 mM NaCl, 10% glycerol). Protein concentration, determined by Pierce BCA method, was adjusted to 1.5–2 mg/ml. Aliquots were stored at −80° C.

Determination of $IC_{50}$:

To determine the IC50 A431 membranes (2.5 mg of protein/sample) pre-treated with EGF (final concentration 200 nM) for 30 min at 4° C. were incubated in 30 ml of reaction buffer (50 mM HEPES pH 7.6, 125 mM NaCl, 12 mM Mg-acetate, 2 mM $MnCl_2$, 1 mM $NaVO_3$, 1 mM ATP, 1 mCi γ-$^{32}$P-ATP) for 1 min at 0° C. in the presence of increasing concentrations of compounds. The reaction was stopped with Laemly solution. The samples were heated 5 min at 95° C. and submitted to SDS-PAGE (7.5% acrylamide gel). Gels were fixed in 40% methanol:10% acetic acid for 1 h and washed overnight with 20% methanol:7% acetic acid. After 15 min in 50% methanol:2% glycerol gels were dried and exposed overnight. Bands corresponding to EGFR were excised from the gels and counted in a β-counter.

Inhibition of cellular tyrosine autophosphorylation (VAP assay)

EGF is able to induce the phosphorylation in tyrosine of a specific set of intracellular proteins including EGFR itself. This increase in tyrosine phosphorylation was measured using the Vectastain-ABC-AP kit (Vector Laboratories) following the manufacturer's instructions. Briefly, 2×$10^4$ A431 cells per well were plated into a microtiter plate and incubated for 3 days at 37° C./5% $CO_2$ until the cultures reached confluency. Cell monolayers were washed with PBS and covered with fresh medium containing 0.1 bovine serum albumin (BSA). Serial dilution of test compounds were added 2 h before the addition of 100 ng/ml EGF; after 10 min stimulation the culture medium was withdrawn, cells were washed 2 times with PBS and fixed for 10 min with cold methanol (−20° C.). After fixation 200 ml of blocking solution (3% BSA in PBS, 0.2% Tween 20, 1% normal horse serum) were added for 1 h at 37° C. Blocking solution was replaced with 3% BSA in PBS containing the antiphosphotyrosine antibody 4G10 (UBI) diluted 1:30000 and incubated for 1 h. Bound antibodies were revealed using the Vectastain-ABC-AP kit with p-nitrophenyl phosphate as the substrate. Reaction was developed for 30 min in the dark and the plates were read at 405 nm.

SRB-Antiproliferative assay (A431 assay)

The antiproliferative activity of the test compounds was assayed on A431 cells using the SRB colorimetric method (P. Skehan et al. : J.Natl.Cancer Inst.1990, 82, 1107–1112). A431 cells were seeded into 96-well microtiter plates (5000 cells/$cm^2$) and incubated overnight at 37° C./5% $CO_2$. Compounds dissolved in DMSO were added in serial dilution and plates were incubated for 3 days at 37° C./5% $CO_2$. Cells were fixed with cold TCA (10% final concentration) and stained with 0.4% Sulforhodamine B dye in 1% acetic acid for 30 min. Dye was solubilized with 10 mM Tris (pH 10.4) and microtiters were read at 550 nm.

The inhibitory activity data for a representative group of compounds according to the present invention, obtained by the AMIKA-, VAP- and A431-assay as described above, are set out in the following Table 1.

TABLE 1

| FCE | AMIKA % of inhibition at | | | VAP | A431 |
|---|---|---|---|---|---|
| | 1 μM | 10 μM | $IC_{50}$ (μM) | $IC_{50}$ (μM) | $IC_{50}$ (μM) |
| 29771 | 93.8 | 98.3 | 0.024 | 0.8 | >1.56 |
| 29772 | 94.9 | 98 | 0.081 | 1.31 | 5.3 |

FCE 29771 means (S)-4-[α-(hydroxymethyl)benzylamino]-6,7dimethoxyquinazoline; and FCE 29772 means (S)-4-[α-(acetoxymethyl)benzylamino]-6,7dimethoxyquinazoline.

As can be appreciated from the activity data shown in Table 1, the compounds according to the invention are endowed with valuable biological properties.

In view of their high activity, the compounds of the invention can be used safely in medicine.

The compounds of the invention can be administered in a variety of dosage forts, e.g. orally, in the forms of tablets, capsules, sugar- and film-coated tablets, liquid solutions or suspensions; rectally, in the form of suppositories; parenterally, e.g. intramuscularly, or by intravenous injection or infusion; or topically. The dosage depends on the age, weight, condition of the patient and administration route. For example, the dosage adopted for oral administration to adult humans for the compound 4-[α-(hydroxymethyl) benzylamino]-6,7-dimethoxyquinazoline may range from about 5 to about 150–200 mg per dose, from 1 to 5 times daily. Of course, these dosage regimes may be adjusted to provide the optimal therapeutic response.

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs;

sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, by means of mixing, granulating, tabletting, sugar-coating or film-coating processes.

The liquid dispersion for oral administration may be, e.g., syrups, emulsions and suspensions.

The syrup may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or, preferably, they may be in the form of sterile aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g. creams, lotions or pastes, can be prepared by admixing the active ingredient with a conventional oleaginous or emulsifying excipient.

A further object of the present invention is a combined method of treatment of cancer or of amelioration of the conditions of mammals, including humans, suffering from cancer, said method comprising administering
1) a compound of the invention, that is a compound of formula (I), (IA) or (IB) or a pharmaceutically acceptable salt thereof, and
2) an additional antitumor agent, in amounts and close enough together in time sufficient to produce a therapeutically useful effect.

The present invention also provides products containing a compound of the invention, that is a compound of formula (I), (IA) or (IB) or a pharmaceutically acceptable salt thereof, and an additional antitumor agent as a combined preparation for simultaneous, separate or sequential use in anticancer therapy.

The term "antitumour agent" is meant to comprise both a single antitumour drug and "cocktails", i.e. a mixture of such drugs, according to the clinical practice.

Examples of antitumour agents that can be formulated with a compound of the invention or, alternatively, can be administered in a combined method of treatment, include doxorubicin, daunomycin, epirubicin, idarubicin, etoposide, fluorouracil, melphalan, cyclophosphamide, bleomycin, vinblastin and mitomycin or a mixture of two or more thereof. The compounds of the invention can therefore be used in a treatment to ameliorate a cancer. They may be administered to a patient suffering from a cancer treatable with an antitumour agent, for example an anthracycline glycoside such as doxorubicin, daunomycin, epirubicin or idarubicin as mentioned above, together with the antitumour agent.

A compound of the invention and an antitumour agent such as an anthracycline glycoside can be administered to improve the condition of a patient having leukemia such as myeloblastic leukemia, lymphoma, sarcoma, neuroblastoma, Wilm's tumour or malignant neoplasm of the bladder, breast, lung or thyroid. Accordingly, the present invention provides a method of treating a patient in need of a tyrosine kinase inhibitor, the method comprising administering to said patient a therapeutically effective amount of a compound of formula (I), (IA) or of formula (IB), as defined above, or a pharmaceutically acceptable salt thereof.

The following examples illustrate but do not limit the invention.

EXAMPLE 1

(S)-4-[α-(hydroxymethyl)benzylamino]-6,7-dimethoxyquinazoline

A solution of 4-chloro-6,7-dimethoxyquinazoline (225 mg, 1 mmol), (S)-2-phenylglycinol (137.2 mg, 1 mmol) and triethylamine (304 mg, 3 mmol) in isopropanol (7 ml) was heated to reflux for about 8 h. Then the mixture was evaporated under vacuum to dryness and the residue purified by gradient elution chromatography on silica gel using as eluant dichloromethane/ethanol 2–6%. Thus pure title compound was obtained in 70% yield (228 mg).

$C_{18}H_{19}N_3O_3$ calcd: C66.45 H5.89 N12.91 found: C66.39 H5.81 N12.88

MS m/z 325

NMR δ ppm (DMSO-$d_3$): 3.79 (m, 2H), 3.87, 3.93 (two s, 6H) 4.96 (t, J=5.7 Hz, 1H), 5.52 (m, 1H), 7.06 (s, 1H), 7.1–7.5 (m, 5H), 7.78 (s, 1H), 8.01 (d, J=8.1 Hz, 1H), 8.24 (s, 1H).

According to the above described procedure the following compounds can be prepared:
(R)-4-[α-(hydroxymethyl)benzylamino]-6,7-dimethoxyquinazoline
$C_{18}H_{19}N_3O_3$ calcd: C66.45 H5.89 N12.91 found: C66.31 H5.75 N12.65

MS m/z 325

NMR δ ppm: 3.79 (m, 2H), 3.87, 3.93 (two s, 6H), 5.02 (t, J=5.7 Hz, 1H), 5.52 (m, 1H), 7.06 (s, 1H), 7.1–7.5 (m, 5H) 7.78 (s, 1H), 8.05 (d, J=8.1 Hz, 1H), 8.24 (s, 1H).
4-[α-(trifluoromethyl)benzylamino]-6,7-dimethoxyquinazoline;
4-[α-(carbamoyl)benzylamino]-6,7-dimethoxyquinazoline;
4-[α-(carbomethoxy)benzylamino]-6,7-dimethoxyquinazoline;
4-[α-(dimethylaminomethyl)benzylamino]-6,7-dimethoxyquinazoline;
4-[α-(hydroxymethyl)-2-tetralylmethylamino]-6,7-dimethoxyquinazoline;
4-[α-(trifluoromethyl)-2-tetralylmethylamino]-6,7-dimethoxyquinazoline;
4-[α-(carbamoyl)-2-tetralylmethylamino]-6,7-dimethoxyquinazoline;
4-[α-(carbomethoxy)-2-tetralylmethylamino]-6,7-dimethoxyquinazoline;
4-[α-(dimethylaminomethyl)-2-tetralylmethylamino]-6,7dimethoxyquinazoline;
(S)-6-[α-(hydroxymethyl)benzylamino]-purine
$C_{13}H_{13}N_5O$ calcd: C61.17 H5.13 N27.43 found: C61.05 H5.05 N27.35

MS m/z 255.

NMR δ ppm: 3.75 (m, 2H), 4.92 (t, J=5.0 Hz, 1H), 5.38 (m, 1H) 7.0–7.5 (m, 5H), 7.77 (d, J=8.3 Hz, 1H), 8.10 (s, 2H), 12.9 (bs, 1H)
6-[α-(trifluoromethyl)benzylamino]-purine;
6-[α-(carbamoyl)benzylamino]-purine;
6-[α-(carbomethoxy)benzylamino]-purine;
6-[α-(dimethylaminomethyl)benzylamino]-purine;
6-[α-(hydroxymethyl)-2-tetralylmethylamino]-purine;
6-[α-(trifluoromethyl)-2-tetralylmethylamino]-purine;
4-[α-(carbamoyl)-2-tetralylmethylamino]-purine;
4-[α-(carbomethoxy)-2-tetralylmethylamino]-purine; and
4-[α-(dimethylaminomethyl)-2-tetralylmethylamino]-purine.

EXAMPLE 2

(S)-4-[α-(acetoxymethyl)benzylamino]-6,7-dimethoxyquinazoline

A solution of (S)-4-[α-(hydroxymethyl)benzylamino]-6,7dimethoxyquinazoline (70 mg, 0.21 mmol) in acetic anhydride (2 ml) was stirred at room temperature for 3 h. Then water was added to the reaction mixture, the precipitate was filtered, washed with water and dried under vacuum. Thus pure title compound was obtained in 90% yield (71 mg).

$C_{20}H_{21}N_3O_4$ calcd: C65.38 H5.76 N11.44 found: C65.18 H5.73 N11.45

MS m/z 367.

NMR δ ppm: 1.95 (s, 3H), 3.88, 3.93 (two s, 6H), 4.42 (m, 2H), 5.30 (m, 1H), 7.09 (s, 1H), 7.2–7.5 (m, 5H), 7.73 (s, 1H), 8.15 (d, J=8.1 Hz, 1H), 8.27 (s, 1H).

According to the above described procedure the following compounds can be prepared:

4-[α-(acetoxymethyl)-2-tetralylmethylamino]-6,7-dimethoxyquinazoline;
6-[α-(acetoxymethyl)benzylamino]-purine; and
6-[α-(acetoxymethyl)-2-tetralylmethylamino]-purine.

EXAMPLE 3

(S)-4-[α-(3-bromobenzoyloxymethyl)benzylamino]-6,7-dimethoxyquinazoline

To a solution of (S)-4-[α-(hydroxymethyl)benzylamino]-6,7-dimethoxyquinazoline (49 mg, 0.15 mmol) in pyridine (2 ml) was added dropwise at 0–5° C. 3-bromobenzoylchloride (33 mg, 0.15 mmol). After 6 h stirring at room temperature the reaction mixture was poured into iced water and extracted with dichloromethane. The organic layer was dried and evaporated to dryness. The residue was purified by flash chromatography on silica gel using as eluant dichloromethane/methanol 95:5 to give pure title compound as a white solid in 71% yield (54 mg).

$C_{25}H_{22}BrN_3O_4$ calcd: C59.07 H4.36 Br15.72 N8.27found: C58.95 H4.15 Br15.65 N8.21

MS m/z 508.

NMR δ ppm: 3.87, 3.91 (two s, 6H), 4.70 (m, 2H), 6.01 (m, 1H), 7.09 (s, 1H), 7.2–7.6 (m, 7H), 7.73 (s, 1H), 7.81 (m, 1H), 7.90 (s, 1H), 8.23 (d, J=8.1 Hz, 1H), 8.28 (s, 1H).

According to the above described procedure the following compounds can be prepared:
(R)-4-[α-(3-bromobenzoyloxymethyl)benzylamino]-6,7-dimethoxyquinazoline;
4-[α-(3-bromobenzoyloxymethyl)-2-tetralylmethylamino]-6,7dimethoxyquinazoline;
6-[cc-(3-bromobenzoyloxymethyl)benzylamino]-purine; and
6-[α-(3-bromobenzoyloxymethyl)-2-tetralylmethylamino]-purine.

EXAMPLE 4

(S)-4-[α-(hydroxymethyl)benzylamino]-6,7-dimethoxyquinazoline hydrochloride salt To a solution of (S)-4-[α-(hydroxymethyl)benzylamino]-6,7dimethoxyquinazoline (325 mg, 1 mmol) in ethanol (2 ml) was added 1N hydrochloric acid (2 ml, 2 mmol) and the resulting mixture was evaporated under vacuum to dryness to give pure title compound in about 100% yield.

$C_{18}H_{20}ClN_3O_3$ calcd: C59.75 H5.57 Cl9.80 N11.61 found: C59.65 H5.51 Cl9.75 N11.63

MS m/z 361.

EXAMPLE 5

(S)-4-[α-(hydroxymethyl)benzylamino]-6,7-dimethoxyquinazoline free base

A suspension of (S)-4-[α-(hydroxymethyl)benzylamino]-6,7dimethoxyquinazoline hydrochloride salt (361.8 mg, 1 mmol) and potassium carbonate (276 mg, 2 mmol) in methanol (6 ml) was stirred at ambient temperature for 0.5 h. The mixture was filtered and the filtrate evaporated under vacuum. The residue was purified by column chromatography on silica gel (eluant dichloromethane/ethanol 2–6%) to give pure title compound in 90% yield.

EXAMPLE 6

4-chloro-6,7-dimethoxyquinazoline

A mixture of 4,5-dimethoxyanthranilic acid (1.97 g, 10 mmol) and formamide (1.0 ml, 25 mmol) was heated to 190° C. for 6 h under stirring. Water (5 ml) was added after cooling to approximately 80° C. and the mixture was stored at room temperature for about 3 h. The precipitate was filtered, washed with water and dried to give 6,7-dimethoxyquinazolin4-one in about 18% yield (0.370 g).

To the above obtained compound (0.370 g, 1.79 mmol) was added thionyl chloride (4 ml) and DMF (1 drop) and the mixture was stirred and heated to reflux for 2 h. After evaporation the mixture was partitioned between ethyl acetate and saturated sodium bicarbonate solution. The organic phase was washed, dried and evaporated to dryness. The residue was purified by column chromatography using increasingly polar mixture of dichloromethane and ethyl acetate. There was thus obtained pure title compound in about 28% yield (0.113 g).

EXAMPLE 7

Tablets each weighing 0.150 g and containing 25 mg of the active substance, can be manufactured as follows:

Composition (for 10,000 tablets):
(S)-4-[α-(hydroxymethyl)benzylamino]-6,7dimethoxyquinazoline
Lactose 800 g
Corn starch 415 g
Talc powder 30 g
Magnesium stearate 5 g The (S)-4-[α-(hydroxymethyl)benzylamino]-6,7-dimethoxyquinazoline, the lactose and half of the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 8

Capsules, each dosed at 0.200 g and containing 20 mg of the active substance can be prepared.

Composition for 500 capsules:
(S)-4-[α-(acetoxymethyl)benzylamino]-6,7dimethoxyquinazoline 10 g
Lactose 80 g
Corn starch 5 g
Magnesium stearate 5 g This formulation is encapsulated in two-piece hard gelatin capsules and dosed at 0.200 g for each capsule.

What is claimed is:

1. A method for inhibiting tyrosine kinase in a mammal comprising administering to said mammal a therapeutically effective amount therefor of a pyrimidine compound of formula (I) or a pharmaceutically acceptable salt thereof

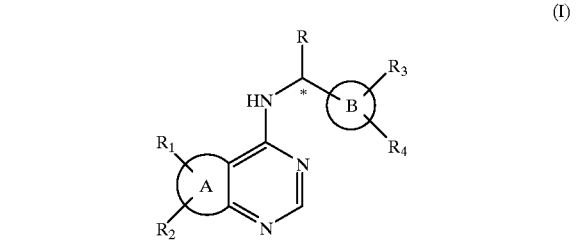

wherein

A is a benzene ring;

B is a benzene, tetralin, indan or 2-oxindole ring;

R is $(C_1-C_4)$perfluoroalkyl, phenyl, phenyl-$(C_1-C_4)$alkyl, hydroxy-$(C_1-C_4)$alkyl, $(C_1-C_4)$alkoxy-$(C_1-C_4)$alkyl, $(C_2-C_4)$acyloxy-$(C_1-C_4)$alkyl, halobenzoyloxy- ($C_1$–$C_4$)alkyl, carboxy, carbamoyl, ($C_1$–$C_4$) alkoxycarbonyl, cyano, ($C_1$–$C_4$)alkylcarbonyl, carboxy-($C_1$–$C_4$)alkyl, carbamoyl-($C_1$–$C_4$)alkyl, ($C_1$–$C_4$)alkoxycarbonyl-($C_1$–$C_4$)alkyl, halo-($C_1$–$C_4$) alkyl, amino-($C_1$–$C_4$)alkyl, mono- or di-($C_1$–$C_4$) alkylamino-($C_1$–$C_4$)alkyl, sulfo-($C_1$–$C_4$)alkyl or sulfamido-($C_1$–$C_4$)alkyl;

each of $R_1$ and $R_2$, which may be the same or different, is hydrogen, $C_1$–$C_4$alkyl, $C_1$–$C_4$alkoxy, halogen or —$NR_5R_6$ in which each of $R_5$ and $R_6$, which may be the same or different is H or $C_1$–$C_4$alkyl; and each of $R_3$ and $R_4$, which may be the same or different, is hydrogen, $C_1$–$C_4$ alkyl, halogen, hydroxy, $C_1$–$C_4$ alkoxy, $C_1$–$C_4$ alkoxycarbonyl, nitro, cyano or $CF_3$.

2. The method according to claim 1, wherein in the compound of formula (I)

B is a benzene or tetralin ring;

R is hydroxy-($C_1$–$C_4$)alkyl, ($C_2$–$C_4$)acyloxy-($C_1$–$C_4$) alkyl, halobenzoyloxy-($C_1$–$C_4$)alkyl, ($C_1$–$C_4$) alkoxycarbonyl, di-($C_1$–$C_4$)alkylamino-($C_1$–$C_4$)alkyl, trifluoromethyl or carbamoyl;

each of $R_1$ and $R_2$, which may be the same or different, is hydrogen or $C_1$–$C_4$ alkoxy; and each of $R_3$ and $R_4$ is hydrogen.

3. The method according to claim 1, wherein the compound of formula (I) is selected from the group consisting of:

4-[α-(hydroxymethyl)benzyilamino]-6,7-dimethoxyquinazoline;

4-[α-(acetoxymethyl)benzylamino]-6,7-dimethoxyquinazoline;

4-[α-(3-bromobenzoyloxymethyl)benzylamino]-6,7-dimethoxyquinazoline;

4-[α-(trifluoromethyl)benzylamino]-6,7-dimethoxyquinazoline;

4-[α-(carbamoyl)benzylamino]-6,7-dimethoxyquinazoline;

4-[α-(carbomethoxy)benzylamino]-6,7-dimethoxyquinazoline;

4-[α-(dimethylaminomethyl)benzylamino]-6,7-dimethoxyquinazoline;

4-[α-(hydroxymethyl)-2-tetrallylmethylamino]-6,7-dimethoxyquinazoline; p1 4-[α-(acetoxymethyl)-2-tetrallylmethylamino]-6,7-dimethoxyquinazoline;

4-[α-(3-bromobenzoyloxymethyl)-2-tetrallylmethylamino]-6,7-dimethoxyquinazoline;

4-[α-(trifluoromethyl)-2-tetralylmethylamino]-6,7-dimethoxyquinazoline;

4-[α-(carbamoyl)-2-tetrallylmethylamino]-6,7-dimethoxyquinazoline;

4-[α-(carbomethoxy)-2-tetrallylmethylamino]-6,7-dimethoxyquinazoline;

4-[α-(dimethylaminomethyl)-2-tetrallylmethylamino]-6,7-dimethoxyquinazoline; and the pharmaceutically acceptable salts thereof; either as single isomers or as a mixture thereof.

4. A method for:

treating epidermal hyperproliferation, as an antimetastatic or anti-cancer agent, to control angiogenesis, inhibit development of atheromatous plaque, treating Alzheimer's disease, or as an immunomodulating agent, in a mammal, comprising administering to said mammal a therapeutically effective amount of a pyrimidine compound of formula (IA) or a pharmaceutically acceptable salt thereof

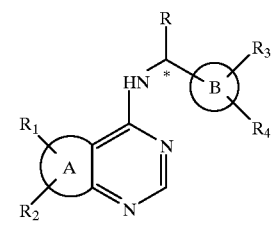

(IA)

wherein

A is a benzene ring;

B is a benzene, tetralin, indan or 2-oxindole ring;

R is ($C_1$–$C_4$)perfluoroalkyl, phenyl, phenyl-($C_1$–$C_4$)alkyl, hydroxy-($C_1$–$C_4$)alkyl, ($C_1$–$C_4$)alkoxy-($C_1$–$C_4$)alkyl, ($C_2$–$C_4$)acyloxy-($C_1$–$C_4$)alkyl, halobenzoyloxy-($C_1$–$C_4$)alkyl, carboxy, carbamoyl, ($C_1$–$C_4$) alkoxycarbonyl, cyano, ($C_1$–$C_4$)alkylcarbonyl, carboxy-($C_1$–$C_4$)alkyl, carbamoyl-($C_1$–$C_4$)alkyl, ($C_1$–$C_4$)alkoxycarbonyl-($C_1$–$C_4$)alkyl, halo-($C_1$–$C_4$) alkyl, amino-($C_1$–$C_4$)alkyl, mono- or di-($C_1$–$C_4$) alkylamino-($C_1$–$C_4$)alkyl, sulfo-($C_1$–$C_4$)alkyl or sulfamido-($C_1$–$C_4$)alkyl;

each of $R_1$ and $R_2$, which may be the same or different, is hydrogen, $C_1$–$C_4$alkyl, $C_1$–$C_4$alkoxy, halogen or —$NR_5R_6$ in which each of $R_5$ and $R_6$, which may be the same or different is H or $C_1$–$C_4$alkyl; and each of $R_3$ and $R_4$, which may be the same or different, is hydrogen, $C_1$–$C_4$ alkyl, halogen, hydroxy, $C_1$–$C_4$ alkoxy, $C_1$–$C_4$ alkoxycarbonyl, nitro, cyano or $CF_3$.

5. The method according to claim 4, wherein the compound of formula (IA)

B is a benzene or tetralin ring;

R is hydroxy-($C_1$–$C_4$)alkyl, ($C_2$–$C_4$)acyloxy-($C_1$–$C_4$) alkyl, halobenzoyloxy-($C_1$–$C_4$)alkyl, ($C_1$–$C_4$) alkoxycarbonyl, di-($C_1$–$C_4$)alkylamino-($C_1$–$C_4$)alkyl, trifluoromethyl or carbamoyl;

each of $R_1$ and $R_2$, which may be the same or different, is hydrogen or $C_1$–$C_4$ alkoxy; and each of $R_3$ and $R_4$ is hydrogen.

6. The method according to claim 4, wherein the compound is selected from the group consisting of:

4-[α-(hydroxymethyl)benzylamino]-6,7-dimethoxyquinazoline;

4-[α-(acetoxymethyl)benzylamino]-6,7-dimethoxyquinazoline;

4-[α-(3-bromobenzoyloxymethyl)benzylamino]-6,7-dimethoxyquinazoline;

4-[α-(trifluoromethyl)benzylamino]-6,7-dimethoxyquinazoline;

4-[α-(carbamoyl)benzylamino]-6,7-dimethoxyquinazoline;

4-[α-(carbomethoxy)benzylamino]-6,7-dimethoxyquinazoline;

4-[α-(dimethylaminomethyl)benzylamino]-6,7-dimethoxyquinazoline;

4-[α-(hydroxymethyl)-2-tetrallylmethylamino]-6,7-dimethoxyquinazoline;

4-[α-(acetoxymethyl)-2-tetrallylmethylamino]-6,7-dimethoxyquinazoline;

4-[α-(3-bromobenzoyloxymethyl)-2-tetrallylmethylamino]-6,7-dimethoxyquinazoline;
4-[α-(trifluoromethyl)-2-tetrallylmethylamino]-6,7-dimethoxyquinazoline;
4-[α-(carbamoyl)-2-tetrallylmethylamino]-6,7-dimethoxyquinazoline;
4-[α-(carbomethoxy)-2-tetrailylmethylamino]-6,7-dimethoxyquinazoline;
4-[α-(dimethylaminomethyl)-2-tetrallylmethylamino]-6,7-dimethoxyquinazoline; and the pharmaceutically acceptable salts thereof, either as single isomers or as a mixture thereof or a pharmaceutically acceptable salt thereof.

7. A pyrimidine compound of formula (IB)

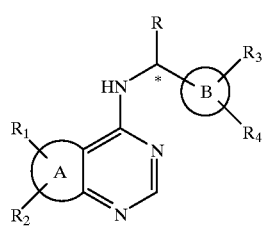

(IB)

wherein
A is a benzene ring;
B is a benzene, tetralin, indan or 2-oxindole ring;
R is (C$_1$–C$_4$)perfluoroalkyl, phenyl, phenyl-(C$_1$–C$_4$)alkyl, hydroxy-(C$_1$–C$_4$)alkyl, (C$_1$–C$_4$)alkoxy-(C$_1$–C$_4$)alkyl, (C$_2$–C$_4$)acyloxy-(C$_1$–C$_4$)alkyl, halobenzoyloxy-(C$_1$–C$_4$)alkyl, carboxy, carbamoyl, (C$_1$–C$_4$)alkoxycarbonyl, cyano, (C$_1$–C$_4$)alkylcarbonyl, carboxy-(C$_1$–C$_4$)alkyl, carbamoyl-(C$_1$–C$_4$)alkyl, (C$_1$–C$_4$)alkoxycarbonyl-(C$_1$–C$_4$)alkyl, halo-(C$_1$–C$_4$)alkyl, amino-(C$_1$–C$_4$)alkyl, mono- or di-(C$_1$–C$_4$)alkylamino-(C$_1$–C$_4$)alkyl, sulfo-(C$_1$–C$_4$)alkyl or sulfamido-(C$_1$–C$_4$)alkyl;
each of R$_1$ and R$_2$, which may be the same or different, is hydrogen, C$_1$–C$_4$alkyl, C$_1$–C$_4$alkoxy, halogen or —NR$_5$R$_6$ in which each of R$_5$ and R$_6$, which may be the same or different is H or C$_1$–C$_4$alkyl; and
each of R$_3$ and R$_4$, which may be the same or different, is hydrogen, C$_1$–C$_4$ alkyl, halogen, hydroxy, C$_1$–C$_4$ alkoxy, C$_1$–C$_4$ alkoxycarbonyl, nitro, cyano or CF$_3$;
and with the proviso that wherein when at the same time, A is unsubstituted benzene, R is hydroxy (C$_1$–C$_2$)alkyl, (C$_1$–C$_4$)alkoxy-(C$_1$–C$_2$)alkyl or (C$_2$–C$_4$)acyloxy-(C$_1$–C$_2$)alkyl, and B is phenyl, then at least one of R$_3$ and R$_4$ is other than hydrogen, halogen, C$_1$–C$_4$ alkyl or C$_1$–C$_4$ alkoxy.

8. A compound according to claim 7 selected from the group consisting of:
4-[α-(hydroxymethyl)benzylamino]-6,7-dimethoxyquinazoline;
4-[α-(acetoxymethyl)benzylamino]-6,7-dimethoxyquinazoline;
4-[α-(3-bromobenzoyloxymethyl)benzylamino]-6,7-dimethoxyquinazoline;
4-[α-(trifluoromethyl)benzylamino]-6,7-dimethoxyquinazoline;
4-[α-(carbamoyl)benzylamino]-6,7-dimethoxyquinazoline;
4-[α-(carbomethoxy)benzylamino]-6,7-dimethoxyquinazoline;
4-[α-(dimethylaininomethyl)benzylamino]-6,7-dimethoxyquinazoline;
4-[α-(hydroxymethyl)-2-tetrallylmethylamino]-6,7-dimethoxyquinazoline;
4-[α-(acetoxymethyl)-2-tetrallylmethylamino]-6,7-dimethoxyquinazoline;
4-[α-(3-bromobenzoyloxymethyl)-2-tetrallylmethylamino]-6,7-dimethoxyquinazoline;
4-[α-(trifluoromethyl)-2-tetrallylmethylamino]-6,7-dimethoxyquinazoline;
4-[α-(carbamoyl)-2-tetrallylmethylamino]-6,7-dimethoxyquinazoline;
4-[α-(carbomethoxy)-2-tetrallylmethylamino]-6,7-dimethoxyquinazoline;
4-[α-(dimethylaminomethyl)-2-tetrallylmethylamino]-6,7-dimethoxyquinazoline; and
the pharmaceutically acceptable salts thereof; either as single isomers or as a mixture thereof or a pharmaceutically acceptable salt thereof.

9. A pharmaceutical composition comprising a pharmaceutically acceptable carrier and/or diluent and as an active principle a compound as defined in claim 7.

10. A process for the preparation of a compound as defined in claim 7, comprising the condensation of a compound of formula (II)

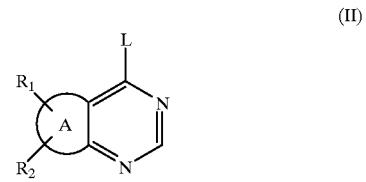

(II)

wherein A, R$_1$ and R$_2$ are as defined in claim 7 and L is a leaving group with an amine compound of formula (III)

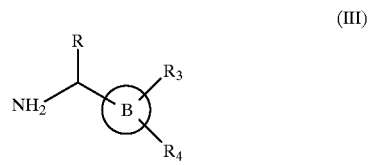

(III)

wherein B, R, R$_3$ and R$_4$ are as defined in claim 7; and, if desired, converting a compound of formula (IB) into another compound of formula (IB), and/or, if desired, converting a compound of formula (IB) into a salt thereof, and/or, if desired, converting a salt of a compound of formula (IB) into a free derivative of formula (IB), and/or, if desired, separating a mixture of isomers of a compound of formula (IB) into the single isomers.

* * * * *